US007534900B2

(12) United States Patent
Ini et al.

(10) Patent No.: US 7,534,900 B2
(45) Date of Patent: May 19, 2009

(54) PROCESS FOR THE PURIFICATION OF DULOXETINE HYDROCHLORIDE

(75) Inventors: Santiago Ini, Haifa (IL); Mili Abramov, Givataim (IL); Anita Liberman, Tel-Aviv (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 30 days.

(21) Appl. No.: 11/376,552

(22) Filed: Mar. 14, 2006

(65) Prior Publication Data

US 2006/0276660 A1 Dec. 7, 2006

Related U.S. Application Data

(60) Provisional application No. 60/773,593, filed on Feb. 14, 2006, provisional application No. 60/736,746, filed on Nov. 14, 2005, provisional application No. 60/726,502, filed on Oct. 12, 2005, provisional application No. 60/661,711, filed on Mar. 14, 2005.

(51) Int. Cl.
C07D 333/12 (2006.01)
(52) U.S. Cl. ............................................. 549/75
(58) Field of Classification Search ............... 549/75
See application file for complete search history.

(56) References Cited

U.S. PATENT DOCUMENTS

| 3,105,564 | A | 10/1963 | Ormond |
| 3,433,804 | A | 3/1969 | Hollinger et al. |
| 3,468,759 | A | * | 9/1969 | Skoda et al. ............ 435/87 |
| 3,814,750 | A | 6/1974 | Cross et al. |
| 4,018,895 | A | 4/1977 | Molloy et al. |
| 4,194,009 | A | 3/1980 | Molloy et al. |
| 4,314,081 | A | 2/1982 | Molloy et al. |
| 4,330,546 | A | 5/1982 | Shepherd |
| 4,956,388 | A | 9/1990 | Robertson et al. |
| 5,023,269 | A | 6/1991 | Robertson et al. |
| 5,362,886 | A | 11/1994 | Berglund |
| 5,491,243 | A | 2/1996 | Berglund |
| 5,508,276 | A | 4/1996 | Anderson et al. |
| 6,541,668 | B1 | 4/2003 | Kjell et al. |
| 2004/0235925 | A1 | 11/2004 | Arneric |
| 2004/0249170 | A1 | 12/2004 | Borghese |
| 2005/0032782 | A1 | 2/2005 | Rao et al. |
| 2006/0270731 | A1 | 11/2006 | Ini et al. |
| 2007/0167636 | A1 | 7/2007 | Butchko et al. |

FOREIGN PATENT DOCUMENTS

| EP | 0 273 658 | 7/1988 |
| EP | 0 457 559 A2 | 11/1991 |
| EP | 0 457 559 A3 | 11/1991 |
| EP | 0 654 264 | 5/1995 |
| EP | 1 506 965 | 2/2005 |
| GB | 1022031 | * 9/1996 |
| WO | WO 03/070720 | 8/2003 |
| WO | WO 2004/009069 | 1/2004 |
| WO | WO 2004/056795 | 7/2004 |
| WO | WO 2004/080468 | 9/2004 |
| WO | WO 2005/019199 | 3/2005 |
| WO | WO 2005/108386 | 11/2005 |
| WO | WO 2006/027798 | 3/2006 |
| WO | WO 2006/045255 | 5/2006 |
| WO | WO 2006/081515 | 8/2006 |
| WO | WO 2006/086809 | 9/2006 |
| WO | WO 2006/099433 | 9/2006 |
| WO | WO 2006/126213 | 11/2006 |
| WO | WO 2007/077580 | 7/2007 |
| WO | WO 2007/096707 | 8/2007 |

OTHER PUBLICATIONS

Abdel-Monem, et al., "N-Demethylation of Morphine And Structurally Related Compounds With Chloroformate Esters", *J. Med. Chem.*, 1972, pp. 208-210, vol. 15, No. 2.
Deeter, et al., "Asymmetric Synthesis And Absolute Stereochemistry Of LY248686", *Tetrahedron Letters*, 1990, pp. 7101-7104, vol. 31, No. 49.
International Search Report PCT/US2006/009247 mailed Jul. 24, 2006.
Kamal, et al., "Chemoenzymatic Synthesis of Duloxetine And Its Enantiomer: Lipase-Catalyzed Resolution Of 3-Hydroxy-3-(2-Thienyl) Propanenitrile", *Tetrahedron Letters*, 2003, pp. 4783-4787, vol. 44, No. 25.
Kometani, et al., "On The Cleavage Of Tertiary Amines With Ethyl Chloroformate", *Chem. Pharm. Bull.*, 1976, pp. 342-349, vol. 24, No. 2.
Wheeler, et al., "An Asymmetric Synthesis of Duloxetine Hydrochloride, a Mixed Uptake Inhibitor of Serotonin and Norepinephrine, and Its C-14 Labeled Isotopomers", *Journal of Labelled Compounds and Radiopharmaceuticals*, 1995, pp. 213-223, vol. 36, No. 3.
International Search Report PCT/US2006/009165 mailed Mar. 14, 2006.
Wheeler, W.J., et al., J. "An Symmetric Synthesis Of Duloxetine Hydrochloride, A Mixed Uptake Inhibitor Of Serotonin And Norepinephrine, And Its C-14 Labeled Isotopomers", Label. Cpds. Radiopharm., 1995, 36, 312.
Fujima, Yoshito et al., "Synthesis of (S)-3-(N-Methylamino)-1-(2-thienyl)propan-1-ol: Revisiting Eli Lilly's Resolution-Racemization-Recycle Synthesis of Duloxetine for Its Robust Processes," *Organic Process Research & Development*, 10(5): 905-913 (2006).
Sakai, K. et al., "Resolution of 3-(methylamino)-1-(2-thienyl)propan-1-ol, a new key intermediate for duloxetine, with (S)-mandelic acid," *Tetrahedron: Asymmetry*, 14(12): 1631-1636 (2003)
ICH Good Manufacturing Practice Guide for Active Pharmaceutical Ingredients, Q7A, Current Step 4 Version, Nov. 10, 2000.
L.A. Sorbera, et al., "Duloxetine Oxalate", *Drugs of the Future*, vol. 25, No. 9, pp. 907-916, (2000).

* cited by examiner

*Primary Examiner*—Taofiq A Solola
(74) *Attorney, Agent, or Firm*—Kenyon & Kenyon LLP

(57) ABSTRACT

Process for the purification of duloxetine HCl is provided.

8 Claims, No Drawings

PROCESS FOR THE PURIFICATION OF DULOXETINE HYDROCHLORIDE

RELATED APPLICATIONS

This application claims benefit of U.S. Provisional Application Nos. 60/726,502, filed Oct. 12, 2005, 60/736,746, filed Nov. 14, 2005, 60/661,711, filed Mar. 14, 2005, and 60/773,593, filed Feb. 14, 2006

FIELD OF THE INVENTION

The present invention relates to a process for the purification of duloxetine hydrochloride.

BACKGROUND OF THE INVENTION

Duloxetine HCl is a dual reuptake inhibitor of the neurotransmitters serotonin and norepinephrine. It is used for the treatment of stress urinary incontinence (SUI), depression, and pain management. It is commercially available as CYMBALTA®. Duloxetine hydrochloride has the chemical name (S)-(+)-N-methyl-3-(1-naphthalenyloxy)-3-(2-thienyl)propanamine hydrochloric acid salt and the following structure.

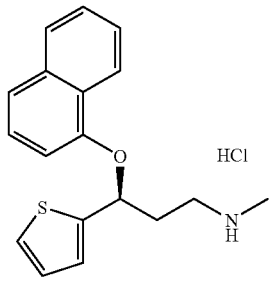

Duloxetine, as well as processes for its preparation, is disclosed in a few published documents, such as U.S. Pat. No. 5,023,269, EP Patent No. 457559 and U.S. Pat. No. 6,541,668.

The conversion of duloxetine to its hydrochloride salt is described in U.S. Pat. No. 5,491,243 and in Wheeler W. J., et al, *J. Label. Cpds.Radiopharm*, 1995, 36, 312. In both cases the reactions are performed in ethyl acetate.

Like any synthetic compound, duloxetine HCl can contain extraneous compounds or impurities that can come from many sources. They can be unreacted starting materials, by-products of the reaction, products of side reactions, or degradation products. Impurities in duloxetine HCl or any active pharmaceutical ingredient (API) are undesirable, and, in extreme cases, might even be harmful to a patient being treated with a dosage form of the API in which a sufficient amount of impurities is present. Furthermore, the undesired enantiomeric impurities reduce the level of the API available in the pharmaceutical composition.

It is also known in the art that impurities in an API may arise from degradation of the API itself, which is related to the stability of the pure API during storage, and the manufacturing process, including the chemical synthesis. Process impurities include unreacted starting materials, chemical derivatives of impurities contained in starting materials, synthetic by-products, and degradation products.

In addition to stability, which is a factor in the shelf life of the API, the purity of the API produced in the commercial manufacturing process is clearly a necessary condition for commercialization. Impurities introduced during commercial manufacturing processes must be limited to very small amounts, and are preferably substantially absent. For example, the ICH Q7A guidance for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of an API, such as duloxetine hydrochloride, it must be analyzed for purity, typically, by HPLC or TLC analysis, to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, is as safe as possible for clinical use. In the United States, the Food and Drug Administration guidelines recommend that the amounts of some impurities be limited to less than 0.1 percent.

Generally, side products, by-products, and adjunct reagents (collectively "impurities") are identified spectroscopically and/or with another physical method, and then associated with a peak position, such as that in a chromatogram or a spot on a TLC plate. (Strobel p. 953, Strobel, H. A.; Heineman, W. R., Chemical Instrumentation: A Systematic Approach, 3rd dd. (Wiley & Sons: New York 1989)).

(+)-N-methyl-3-(1-naphthalenyloxy)-3-(3-thienyl)propanamine is disclosed by Olsen B. A et al, as an impurity obtained in the preparation of duloxetine (J. Lib. Chrom. & Rel. Technol, 1996, 19, 1993).

There is a need in the art for a process for preparing chemically and/or enantiomerically pure duloxetine HCl

SUMMARY OF THE INVENTION

The present invention encompasses a process for the purification of duloxetine HCl, comprising crystallizing duloxetine HCl in water, or a solvent selected from the group consisting of $C_{3-8}$ ketones, $C_{3-8}$ esters, $C_{2-8}$ ethers, $C_{2-8}$ alcohols, and mixtures thereof with water.

DETAILED DESCRIPTION OF THE INVENTION

As used herein the term "crystallizing" refers to a process comprising: heating a mixture of a starting material and a solvent to a temperature of between about 10° C. below and above the reflux temperature of the solvent to obtain a solution, and cooling the solution to a temperature of about 0° C. to about 30° C.

The present invention encompasses a process for the purification of duloxetine HCl, comprising crystallizing duloxetine HCl in water or a solvent selected from the group consisting of $C_{3-8}$ ketones, $C_{3-8}$ esters, $C_{2-8}$ ethers, $C_{2-8}$ alcohols, and mixtures thereof with water.

Preferably, the solvent is selected from the group consisting of acetone, methyl ethyl ketone (MEK), ethyl acetate, methyl t-butyl ether (MTBE), ethanol, isopropanol, and n-butanol. Most preferably, the solvent is a mixture of acetone and water or isopropanol.

Preferably, when the solvent is in a mixture with water, the ratio (vol/vol) of the solvent and water is about 97:3 to about 98.25:1.75. Preferably, the ratio is at least about 98:2. Preferably, the ratio (vol/vol) of the starting material and the water or solvent is about 1:10. Preferably, the dissolution occurs at reflux temperature. Preferably, after cooling, the solution is maintained while stirring, for about 10 minutes to about 24 hours.

Preferably, the duloxetine HCl obtained after the crystallization is purer than the duloxetine HCl starting material. To exemplify, the obtained duloxetine HCl contains a lower level of the impurity (+)-N-methyl-3-(1-naphthalenyloxy)-3-(3-thienyl)propanamine (DLX-ISO3) and a lower level of the R-enantiomer of duloxetine.

The crystallization process may be repeated in order to increase the purification even further either with the same or a different solvent that was used for the first crystallization.

Having described the invention with reference to certain preferred embodiments, other embodiments will become apparent to one skilled in the art from consideration of the specification. The invention is further defined by reference to the following examples, describing in detail the analysis of the duloxetine HCl and methods for preparing the duloxetine HCl of the invention.

It will be apparent to those skilled in the art that many modifications, both to materials and methods, may be practiced without departing from the scope of the invention.

EXAMPLES

HPLC Method for Measuring Chemical Purity:

Column: Hypersyl Gold (150×4.6 5µ)

Mobile phase: (A) 63% ($KH_2PO_4$ (0.02M) pH-2.5): 37% (35% MeOH:10% THF) (B) 20% ($KH_2PO_4$ (0.02M) pH-2.5): 80% ACN Gradient: From 0 to 15 min (A) isocraticaly From 15 to 60 min (B) increases from 0 to 100%

Detection: 230 nm

Flow: 1 mL/min

Detection limit: 0.02%

HPLC Method for Measuring Enantiomeric Purity:

Column: Diacel Chiral OD 250×4.6 5µ

Eluent: Hexane (900 mL):IPA (100 mL): DEA(2 mL)

Flow: 1 mL/min

Detection: 230 nm

Sample conc: 0.5 mg/mL

Sample vol: 100 µL

Column temp: 20° C.

Detection limit: 0.02%

Example 1

Purification of Duloxetine Hydrochloride in Acetone/Water

Example 1a

A mixture of 20 g Duloxetine hydrochloride in 204 ml acetone/water (98:2) was heated to reflux. After the compound was dissolved, the oil bath was removed, and the solution was cooled to 15° C. overnight. The solid was filtered, washed with acetone, and dried in a vacuum oven at 45° C. for 16 hours, giving Duloxetine hydrochloride (78 percent yield) containing DLX-ISO3 (0.21 percent) and enantiomer R(<0.03 percent)

Example 1b

A mixture of 13 g of the previously obtained Duloxetine hydrochloride in 130 ml acetone/water (98:1.5) was heated to reflux. After the compound was dissolved, the oil bath was removed, and the solution was cooled to 10° C. for 2 hours. The solid was filtered, washed with acetone, and dried in a vacuum oven at 45° C. for 16 hours, giving Duloxetine hydrochloride (87 percent yield) containing DLX-ISO3 (0.15 percent) and free of enantiomer R.

Example 1c

A mixture of 10 g of the previously obtained Duloxetine hydrochloride in 100 ml acetone/water (98:2) was heated to reflux. After the compound was dissolved, the oil bath was removed, and the solution was cooled to room temperature and stirred for 1 hour. The solid was filtered, washed with acetone, and dried in a vacuum oven at 45° C. for 16 hours, giving Duloxetine hydrochloride (80 percent yield) containing DLX-ISO3 (0.07 percent), and free of enantiomer R.

Example 1d

A mixture of 7.5 g of the previously obtained Duloxetine hydrochloride in 75 ml acetone/water (98:2) was heated to reflux. After the compound was dissolved, the oil bath was removed, and the solution was cooled to room temperature and stirred for 2 hours. The solid was filtered, washed with acetone, and dried in a vacuum oven at 40° C. for 16 hours, giving Duloxetine hydrochloride (73 percent yield) containing DLX-ISO3 (0.03 percent), and free of enantiomer R.

Example 2

Purification of Duloxetine Hydrochloride in Acetone/Water Under Different Conditions Example 2a A mixture of 16 g Duloxetine hydrochloride (contaminated with 0.30 percent DLX-ISO3 and 0.13 percent enantiomer R) in 160 ml acetone was heated to reflux, and then 4 ml of water were added till complete dissolution. After the compound was dissolved, the oil bath was removed, and the solution was cooled to room temperature and stirred for one hour. The solid was filtered, washed with acetone, and dried in a vacuum oven at 45° C. for 16 hours, giving Duloxetine hydrochloride (68 percent yield) containing DLX-ISO3 (0.10 percent) and free of enantiomer R.

Example 2b

A mixture of 8 g of the previously obtained Duloxetine hydrochloride in 80 ml acetone was heated to reflux, and 2 ml of water were added. After the compound was dissolved, the oil bath was removed, and the solution was cooled to room temperature and stirred for half hour. The solid was filtered, washed with acetone, and dried in a vacuum oven at 45° C. for 16 hours, giving Duloxetine hydrochloride (36 percent yield) containing DLX-ISO3 (0.06 percent).

Example 2c

A mixture of 2 g of the previously obtained Duloxetine hydrochloride in 20 ml of acetone was heated to reflux, and 0.4 ml of water were added. After the compound was dissolved, the oil bath was removed, and the solution was cooled to room temperature and stirred for three hours. The solid was filtered, washed with acetone, and dried in a vacuum oven at 45° C. for 16 hours, giving Duloxetine hydrochloride (50 percent yield) free of DLX-ISO3.

Example 3

Purification of Duloxetine Hydrochloride in Ethyl Acetate

A mixture of 2 g Duloxetine hydrochloride (contaminated with 0.46 percent DLX-ISO3 and 0.13 percent enantiomer R) in 10 ml ethyl acetate was heated to reflux, and 50 ml of ethyl acetate were added. The mixture was stirred at the same temperature for 40 minutes, followed by cooling to room temperature and stirring for two hours. The solid was filtered, washed with ethyl acetate, and dried in a vacuum oven at 45° C. for 16 hours, giving Duloxetine hydrochloride (93 percent yield) containing DLX-ISO3 (0.28 percent) and 0.07 percent of enantiomer R.

Example 3 was repeated to yield Duloxetine hydrochloride containing less than 0.14 percent DLX-ISO3.

Example 4

Purification of Duloxetine Hydrochloride in IPA

Example 4a

A mixture of 8.4 g Duloxetine hydrochloride (contaminated with 0.29 percent DLX-ISO3 and 0.17 percent enantiomer R) in 84 ml IPA was heated to reflux. The solution was stirred at the same temperature for 15 minutes, followed by cooling to room temperature and stirring for two hours. The solid was filtered, washed with IPA, and dried in a vacuum oven at 45° C. for 16 hours, giving Duloxetine hydrochloride (62 percent yield) containing DLX-ISO3 (0.21 percent) and free of enantiomer R.

Example 4b

A mixture of 8.8 g Duloxetine hydrochloride (contaminated with 0.21 percent DLX-ISO3) in 70 ml IPA was heated to reflux. The solution was stirred at the same temperature for 15 minutes, followed by cooling to room temperature and stirring for two hours. The solid was filtered, washed with IPA, and dried in a vacuum oven at 45° C. for 16 hours, giving Duloxetine hydrochloride (83 percent yield) containing DLX-ISO3 (0.17 percent).

Example 4c

A mixture of 5 g Duloxetine hydrochloride (contaminated with 0.17 percent DLX-ISO3) in 40 ml IPA was heated to reflux. The solution was stirred at the same temperature for 15 minutes, followed by cooling to room temperature and stirring for two hours. The solid was filtered, washed with IPA, and dried in a vacuum oven at 45° C. for 16 hours, giving Duloxetine hydrochloride (65 percent yield) containing DLX-ISO3 (0.13 percent)

Example 5

Purification of Duloxetine Hydrochloride in MTBE/Water

Example 5a

A mixture of 12 g Duloxetine hydrochloride (contaminated with 0.29 percent DLX-ISO3 and 0.11 percent enantiomer) in 120 ml MTBE was heated to reflux, and 3.6 ml of water were added until complete dissolution. The two phase solution was stirred at the same temperature for 15-30 minutes, followed by cooling to room temperature and stirring overnight. The solid was filtered, washed with the same solvents, and dried in a vacuum oven at 45° C. for 16 hours, giving Duloxetine hydrochloride (29 percent yield) containing DLX-ISO3 (0.16 percent) and less than 0.02 percent of enantiomer R.

Example 5b

A mixture of 2 g Duloxetine hydrochloride (contaminated with 0.16 percent DLX-ISO3 and less than 0.03 percent of enantiomer R) in 20 ml MTBE is heated to reflux, and 0.36 ml of water are added until complete dissolution. The two phase solution is stirred at the same temperature for 15 to 30 minutes, followed by cooling to room temperature and stirring overnight. The solid is filtered, washed with the same solvents, and dried in a vacuum oven at 45° C. for 16 hours, giving Duloxetine hydrochloride (29 percent yield).

Example 6

Purification of Duloxetine Hydrochloride in MEK/Water

Example 6a

A mixture of 4 g Duloxetine hydrochloride (contaminated with 0.30 percent DLX-ISO3 and 0.17 percent enantiomer R) in 20 ml MEK was heated to reflux, and 0.6 ml of water were added until complete dissolution. The solution was stirred at the same temperature for 15-30 minutes, followed by cooling to 0° to 5° C. and stirring for two hours. The solid was filtered, washed with the same solvents, and dried in a vacuum oven at 45° C. for 16 hours, giving Duloxetine hydrochloride (32 percent yield) containing DLX-ISO3 (0.10 percent) and free of enantiomer R.

Example 6b

A mixture of 0.5 g Duloxetine hydrochloride (contaminated with 0.10 percent DLX-ISO3) in 2.5 ml MEK is heated to reflux, and 0.1 ml of water are added until complete dissolution. The solution is stirred at the same temperature for 15 to 30 minutes, followed by cooling to 0° to 5° C. and stirring for two hours. The solid is filtered, washed with the same solvents, and dried in a vacuum oven at 45° C. for 16 hours, giving Duloxetine hydrochloride (32 percent yield).

Example 7

Purification of Duloxetine Hydrochloride in Water

A mixture of 2.7 g Duloxetine hydrochloride (contaminated with 0.50 percent DLX-ISO3 and 0.29 percent enantiomer R) in 27 ml water was heated to reflux. The solution was stirred at the same temperature for 10 to 15 minutes, followed by cooling to room temperature and stirring overnight. The solid was filtered, washed with water, and dried in a vacuum oven at 45° C. for 16 hours, giving Duloxetine hydrochloride (61 percent yield) containing DLX-ISO3 (0.25 percent) and free of enantiomer R.

Example 7 is repeated to yield Duloxetine hydrochloride containing less than 0.14 percent DLX-ISO3.

Example 8

Purification of Duloxetine Hydrochloride in MEK

A mixture of 2 g Duloxetine hydrochloride (contaminated with 0.26 percent DLX-ISO3 and 0.17 percent enantiomer R) in 40 ml MEK was heated to reflux. The solution was stirred at the same temperature for 30 minutes, followed by cooling to 0° to 5° C. and stirring for 2 hours. The solid was filtered, washed with MEK, and dried in a vacuum oven at 45° C. for 16 hours, giving Duloxetine hydrochloride (60 percent yield) contaminated with DLX-ISO3 (0.21 percent) and free of enantiomer R.

Example 8 is repeated to yield Duloxetine hydrochloride containing less than 0.14 percent DLX-ISO3.

Example 9

Purification of Duloxetine Hydrochloride in Acetone

Example 9a

A mixture of 2 g Duloxetine hydrochloride (contaminated with 0.46 percent DLX-ISO3 and 0.13 percent enantiomer R) in 130 ml acetone was heated to reflux. The solution was stirred at the same temperature for one hour, followed by cooling to 27° C. The solid was filtered at the same temperature, and dried in a vacuum oven at 45° C. for 16 hours, giving Duloxetine hydrochloride (59.50 percent yield) containing DLX-ISO3 (0.17 percent) and free of enantiomer R.

Example 9b

A mixture of 1 g Duloxetine hydrochloride (contaminated with 0.17 percent DLX-ISO3) in 65 ml acetone was heated to reflux. The solution was stirred at the same temperature for one hour, followed by cooling to 27° C. The solid was filtered at the same temperature, and dried in a vacuum oven at 45° C. for 16 hours, giving Duloxetine hydrochloride (59.50 percent yield).

Example 10

Purification of Duloxetine Hydrochloride in n-butanol

A mixture of 2 g Duloxetine hydrochloride (contaminated with 0.26 percent DLX-ISO3 and 0.17 percent enantiomer R) in 12 ml n-butanol was heated to reflux. The solution was stirred at the same temperature for 10 minutes, followed by cooling to room temperature and stirring for 1 hour. The solid was filtered, washed with n-butanol, and dried in a vacuum oven at 45° C. for 16 hours, giving Duloxetine hydrochloride (75 percent yield) containing DLX-ISO3 (0.24 percent, prophetic data) and 0.07 percent of enantiomer R.

Example 10 is repeated, using a solvent selected from: $C_{3-5}$ ketones, $C_{3-5}$ esters, $C_{2-5}$ ethers, $C_{2-4}$ alcohols other than n-butanol and mixtures thereof with water to yield Duloxetine hydrochloride containing less than 0.14 percent DLX-ISO3.

Example 11

Purification of Duloxetine Hydrochloride in Ethanol

A mixture of 2.22 g Duloxetine hydrochloride (contaminated with 0.28 percent DLX-ISO3 and 0.50 percent enantiomer R) in 22.2 ml ethanol was heated to reflux. The solution was stirred at the same temperature for 15 minutes, followed by cooling to room temperature and stirring for 1 hour. The solid was filtered, washed with n-butanol, and dried in a vacuum oven at 45° C. for 16 hours, giving Duloxetine hydrochloride (36 percent yield) containing DLX-ISO3 (0.21 percent) and free of enantiomer R.

Example 11 is repeated to yield Duloxetine hydrochloride containing less than 0.14 percent DLX-ISO3.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

What is claimed:

1. A process for the purification of duloxetine HCl, comprising crystallizing duloxetine HCl in water or a solvent selected from the group consisting of $C_{3-8}$ ketones, $C_{3-8}$ esters, $C_{2-8}$ ethers, $C_{2-8}$ alcohols, and mixtures thereof with water.

2. The process of claim 1, wherein the solvent is selected from the group consisting of acetone, methyl ethyl ketone (MEK), ethyl acetate, methyl t-butyl ether (MTBE), ethanol, isopropanol, and n-butanol.

3. The process of claim 1, wherein the solvent is isopropanol or a mixture of acetone and water.

4. The process of any of claims 1 to 3, wherein the ratio (vol/vol) of the solvent and water is at least about 97:3 to about 98.25:1.75.

5. The process of claim 4, wherein the ratio (vol/vol) of the solvent and water is at least about 98:2.

6. The process of any of claims 1 to 3, wherein the ratio (vol/vol) of the starting duloxetine HCl and the water or solvent is about 1:10.

7. The process of claim 1, further comprising dissolving starting duloxetine HCl in water or the solvent at reflux temperature.

8. The process of claim 1, further comprising cooling the duloxeting HCl in water or the solvent, and after cooling, maintaining the solution while stirring for about 10 minutes to about 24 hours.

* * * * *

(12) EX PARTE REEXAMINATION CERTIFICATE (9819th)
United States Patent
Ini et al.

(10) Number: US 7,534,900 C1
(45) Certificate Issued: Aug. 28, 2013

(54) PROCESS FOR THE PURIFICATION OF DULOXETINE HYDROCHLORIDE

(75) Inventors: Santiago Ini, Haifa (IL); Mili Abramov, Givataim (IL); Anita Liberman, Tel-Aviv (IL)

(73) Assignee: Teva Pharmaceuticals USA, Inc., North Wales, PA (US)

Reexamination Request:
No. 90/012,668, Sep. 15, 2012

Reexamination Certificate for:
Patent No.: 7,534,900
Issued: May 19, 2009
Appl. No.: 11/376,552
Filed: Mar. 14, 2006

Related U.S. Application Data

(60) Provisional application No. 60/726,502, filed on Oct. 12, 2005, provisional application No. 60/736,746, filed on Nov. 14, 2005, provisional application No. 60/661,711, filed on Mar. 14, 2005, provisional application No. 60/773,593, filed on Feb. 14, 2006.

(51) Int. Cl.
*C07D 333/12* (2006.01)

(52) U.S. Cl.
USPC .......................................................... 549/75

(58) Field of Classification Search
None
See application file for complete search history.

(56) References Cited

To view the complete listing of prior art documents cited during the proceeding for Reexamination Control Number 90/012,668, please refer to the USPTO's public Patent Application Information Retrieval (PAIR) system under the Display References tab.

*Primary Examiner* — Sharon Turner

(57) ABSTRACT

Process for the purification of duloxetine HCl is provided.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-2 and 6-8 are cancelled.

Claims 3-5 were not reexamined.

\* \* \* \* \*